United States Patent
Emadi et al.

(10) Patent No.: US 9,851,250 B1
(45) Date of Patent: Dec. 26, 2017

(54) FULLY INTEGRATED GAS CONCENTRATION SENSOR

(71) Applicant: Maxim Integrated Products, Inc., San Jose, CA (US)

(72) Inventors: Arvin Emadi, San Jose, CA (US); Arkadii V. Samoilov, Saratoga, CA (US); Nicole D. Kerness, Ithaca, NY (US)

(73) Assignee: Maxim Integrated Products, Inc., San Jose, CA (US)

( * ) Notice: Subject to any disclaimer, the term of this patent is extended or adjusted under 35 U.S.C. 154(b) by 0 days.

(21) Appl. No.: 15/359,095

(22) Filed: Nov. 22, 2016

Related U.S. Application Data

(60) Provisional application No. 62/259,924, filed on Nov. 25, 2015, provisional application No. 62/267,587, filed on Dec. 15, 2015.

(51) Int. Cl.
*G01N 21/3504* (2014.01)
*G01J 3/26* (2006.01)
(Continued)

(52) U.S. Cl.
CPC .............. *G01J 3/108* (2013.01); *G01J 3/26* (2013.01); *G01J 3/42* (2013.01); *G01N 21/3504* (2013.01); *G01N 2201/068* (2013.01)

(58) Field of Classification Search
CPC ............. G01N 21/3504; G01N 21/031; G01N 21/552; G01N 2021/3133; G01J 3/26; G01J 3/42; G01J 3/108
See application file for complete search history.

(56) References Cited

U.S. PATENT DOCUMENTS

| 4,479,866 A * | 10/1984 | Sone | G01N 27/4071 204/425 |
| 2007/0102639 A1 * | 5/2007 | Cutler | G01N 21/3504 250/339.13 |

(Continued)

OTHER PUBLICATIONS

Quick Guide for CO2 Waveforms, PROPAQ® Vital Signs Monitors, Welch Allyn, Beverton, Oregon USA, 2001, P/N: 810-0466-02 Rev A 11/01, pp. 1-8.

*Primary Examiner* — David Porta
*Assistant Examiner* — Faye Boosalis
(74) *Attorney, Agent, or Firm* — Advent, LLP

(57) ABSTRACT

A gas concentration sensor is includes an integrated die-form electromagnetic radiation source and an integrated die-form infrared detector. In one or more implementations, the gas concentration sensor includes a package substrate defining at least one aperture, a gas permeable mesh coupled to the package substrate and covering at least a portion of the at least one aperture, a die-form electromagnetic radiation source positioned in an interior region of the package substrate, a die-form detector positioned in the interior region of the package substrate, and control circuitry operably coupled to the die-form detector and configured to detect and calibrate one or more signal outputs from the die-form detector to determine a gas concentration within the interior region of the package substrate. The gas concentration sensor can be configured for specific detection of various gases through control of the spectral wavelengths emitted by the electromagnetic radiation source(s) and/or detected by the detector(s).

20 Claims, 14 Drawing Sheets

(51) Int. Cl.
    *G01J 3/42*      (2006.01)
    *G01J 3/10*      (2006.01)

(56) References Cited

U.S. PATENT DOCUMENTS

| | | | |
|---|---|---|---|
| 2010/0265078 A1* | 10/2010 | Friedman | G01T 1/26 340/600 |
| 2011/0009752 A1* | 1/2011 | Chen | A61B 5/0066 600/478 |
| 2014/0116122 A1* | 5/2014 | Lammel | G01L 19/0092 73/73 |

* cited by examiner

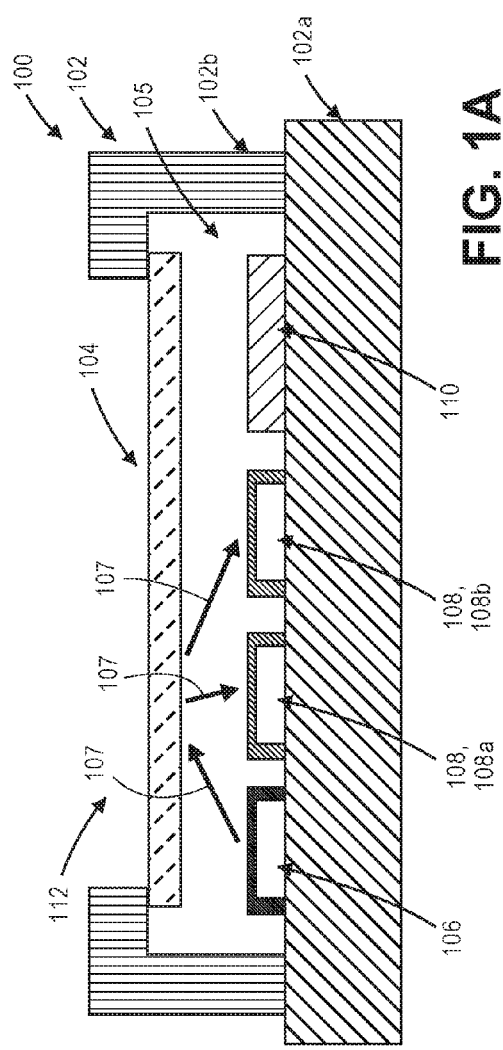
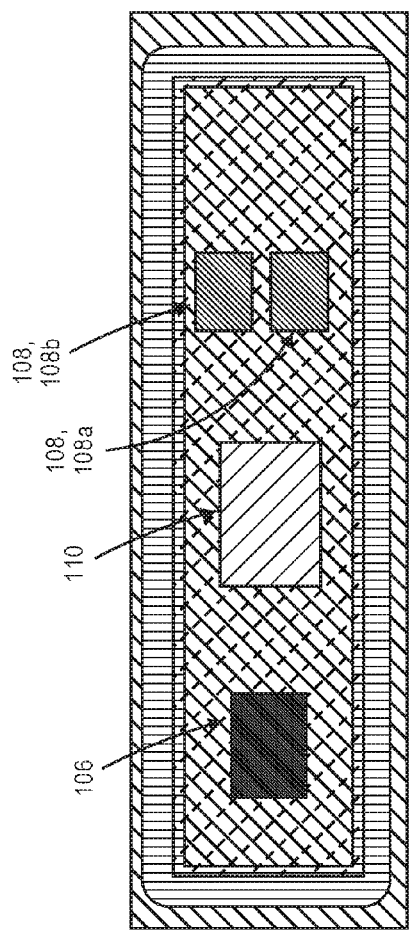

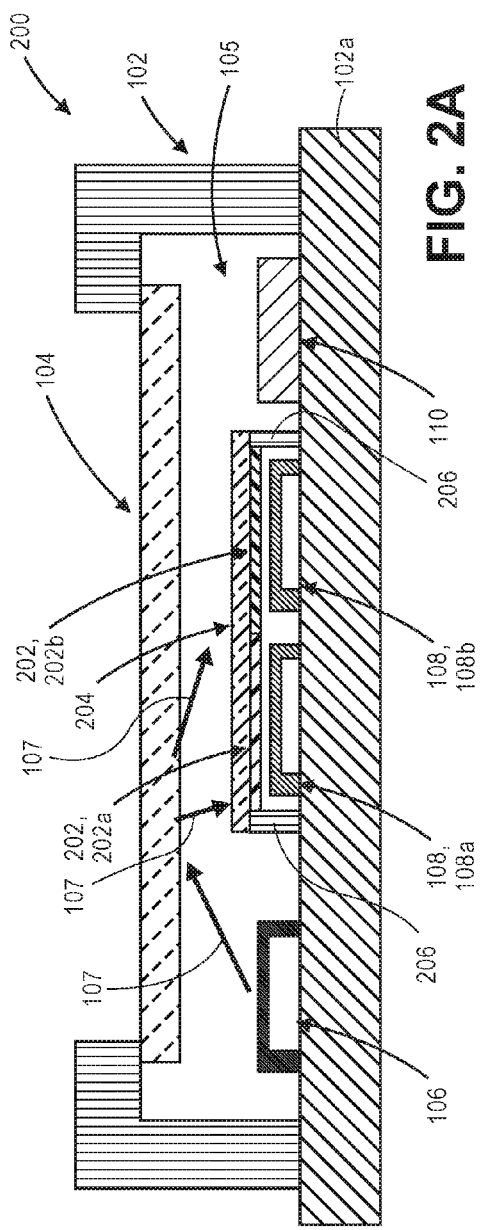
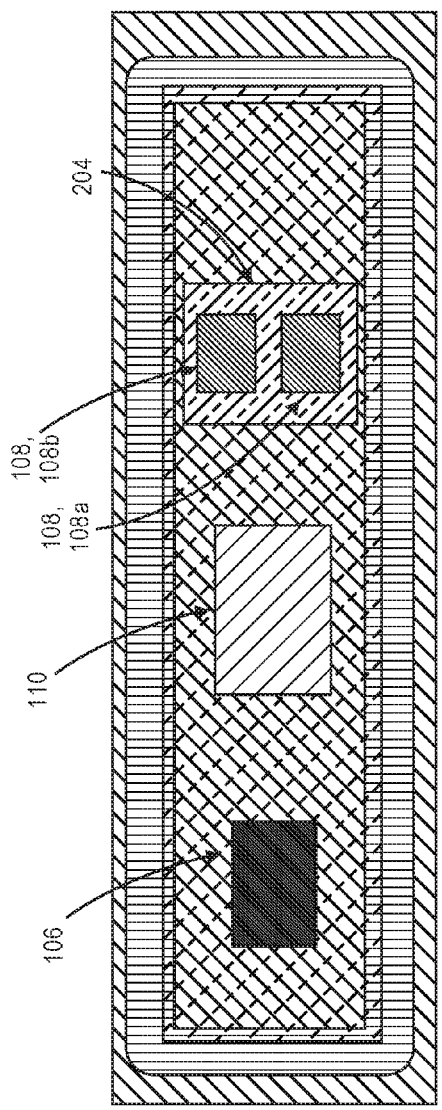

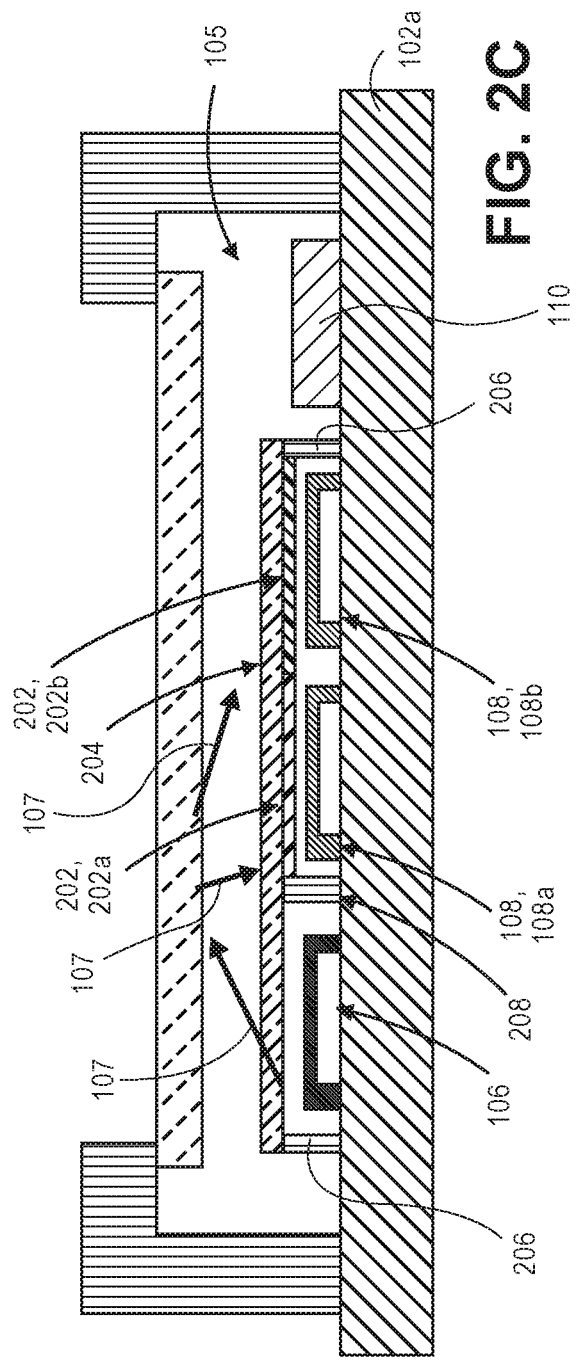

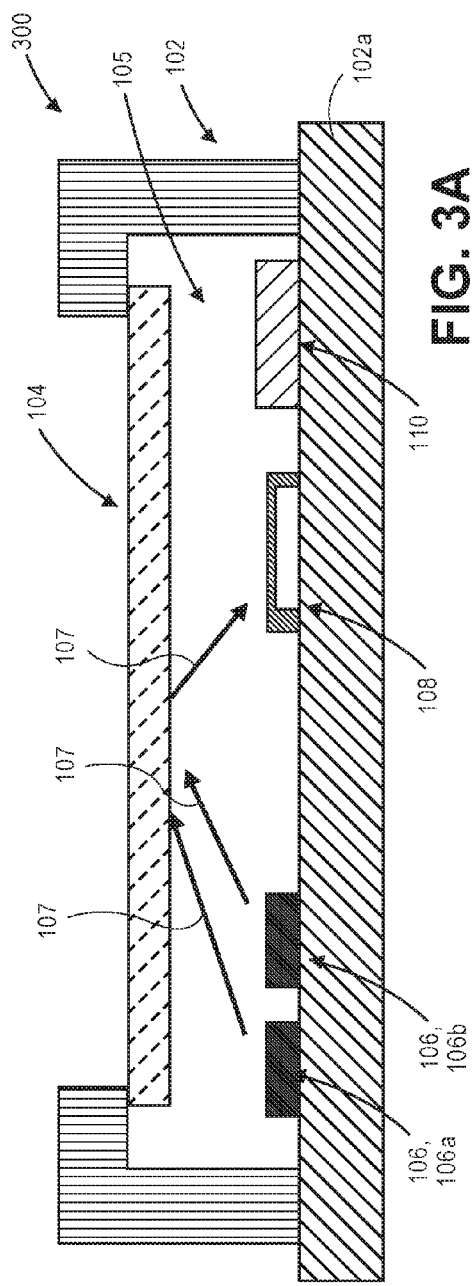
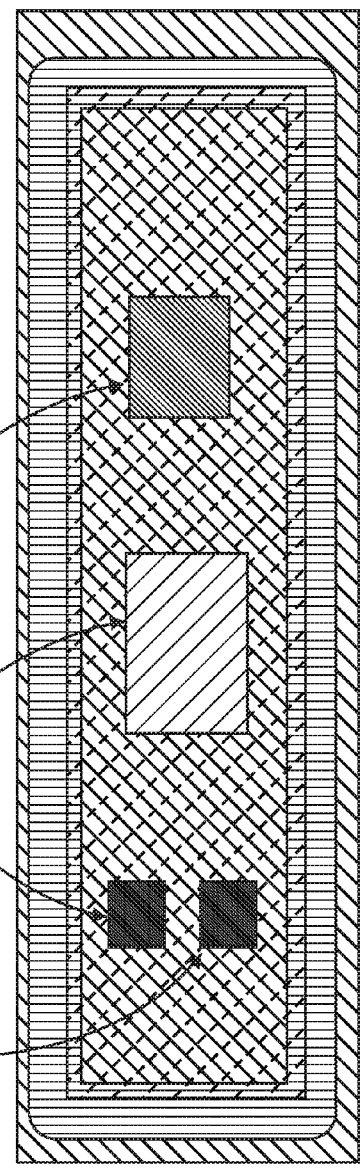
FIG. 3A
FIG. 3B

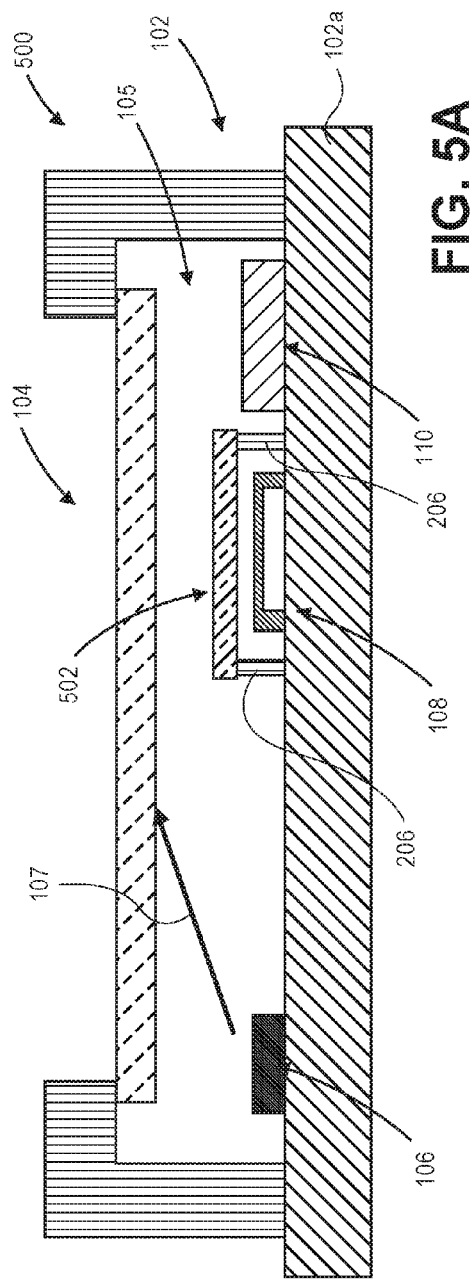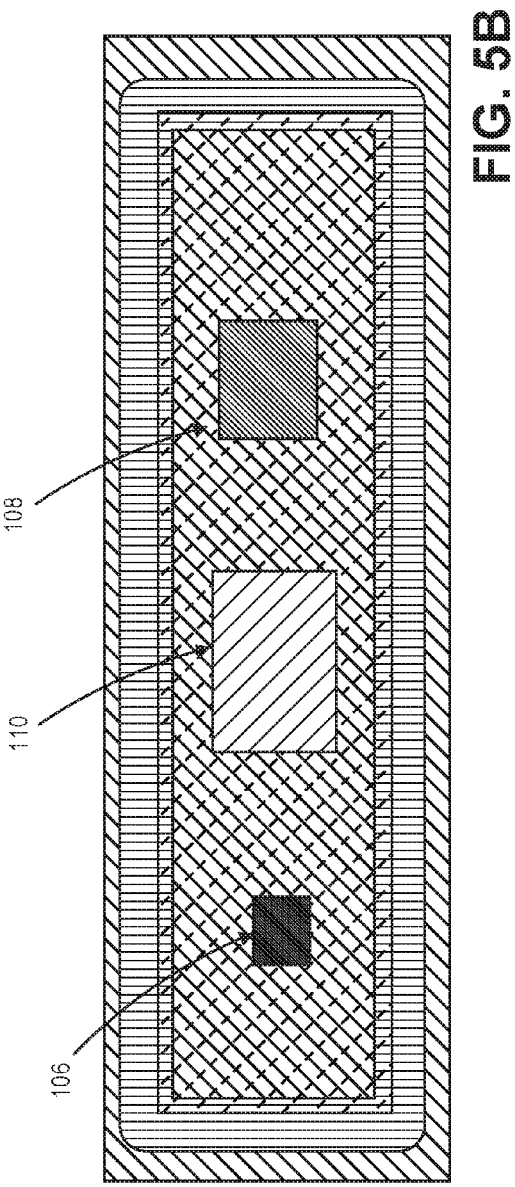

FULLY INTEGRATED GAS CONCENTRATION SENSOR

CROSS-REFERENCE TO RELATED APPLICATIONS

The present application claims the benefit under 35 U.S.C. §119(e) of U.S. Provisional Application Ser. No. 62/259,924, entitled FULLY INTEGRATED GAS CONCENTRATION SENSOR, filed Nov. 25, 2015, and of U.S. Provisional Application Ser. No. 62/267,587, entitled FULLY INTEGRATED GAS CONCENTRATION SENSOR, filed Dec. 15, 2015. U.S. Provisional Application Ser. Nos. 62/259,924 and 62/267,587 are hereby incorporated by reference in their entirety.

BACKGROUND

A gas sensor or gas concentration sensor is a subclass of chemical sensors that measures the concentration of gases in the vicinity of the sensor. A gas interacts with the sensor and provides a measure of the concentration of the gas based on a signal or property change created by the interaction. Gas sensors can include sensors based on measuring changes in electrical properties of the sensor, such as, but not limited to, metal oxide semiconductor sensors, polymer coating based sensors, carbon nanotube based sensors, and moisture adsorbing material based sensors. Other types of gas sensors can include sensors based on measuring other properties, such as, but not limited to, optical, acoustic, gravimetric, gas chromatograph, flame ionization, and calorimetric based sensors.

SUMMARY

A gas concentration sensor is described having an integrated die-form light source and an integrated die-form infrared detector. In one or more implementations, the gas concentration sensor includes a package substrate defining at least one aperture, a gas permeable mesh coupled to the package substrate and covering at least a portion of the at least one aperture, a die-form light source positioned in an interior region of the package substrate, a die-form detector positioned in the interior region of the package substrate, and control circuitry operably coupled to the die-form detector and configured to detect and calibrate one or more signal outputs from the die-form detector to determine a gas concentration within the interior region of the package substrate. The control circuitry can be connected to the die-form light source to drive the voltage or current according to specific timings. The gas concentration sensor can be configuration for specific detection of various gases through control of the spectral wavelengths emitted by the light source(s) and/or detected by the detector(s).

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

The Detailed Description is described with reference to the accompanying figures. The use of the same reference numbers in different instances in the description and the figures may indicate similar or identical items.

FIG. 1A illustrates a side view of a fully integrated gas concentration sensor in accordance with an embodiment of this disclosure.

FIG. 1B illustrates a top view of a fully integrated gas concentration sensor in accordance with an embodiment of this disclosure.

FIG. 2A illustrates a side view of a fully integrated gas concentration sensor having one or more filters in accordance with an embodiment of this disclosure.

FIG. 2B illustrates a top view of a fully integrated gas concentration sensor having one or more filters in accordance with an embodiment of this disclosure.

FIG. 2C illustrates a side view of a fully integrated gas concentration sensor having a light source in a same package as one or more detectors having one or more filters in accordance with an embodiment of this disclosure.

FIG. 3A illustrates a side view of a fully integrated gas concentration sensor having a plurality of light sources in accordance with an embodiment of this disclosure.

FIG. 3B illustrates a top view of a fully integrated gas concentration sensor having a plurality of light sources in accordance with an embodiment of this disclosure.

FIG. 5A illustrates a side view of a fully integrated gas concentration sensor having a tunable filter adjacent a broadband detector in accordance with an embodiment of this disclosure.

FIG. 5B illustrates a top view of a fully integrated gas concentration sensor having a tunable filter adjacent a broadband detector in accordance with an embodiment of this disclosure.

DETAILED DESCRIPTION

Overview

Figure 4A:
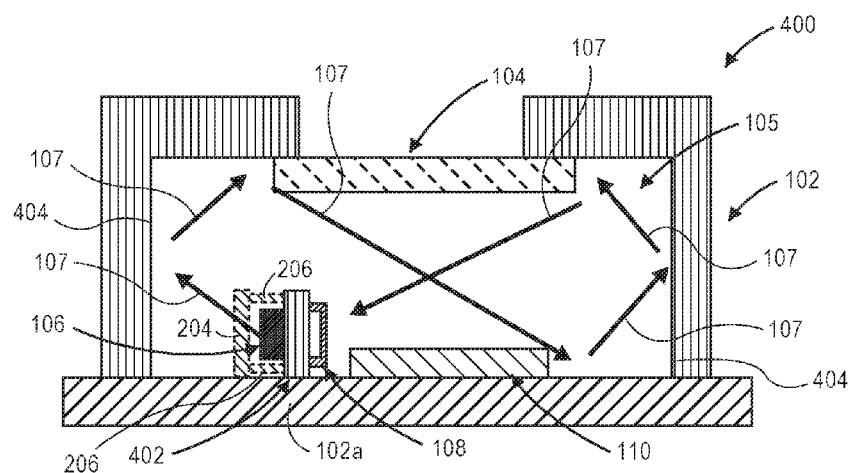
FIG. 4A illustrates a side view of a fully integrated gas concentration sensor having a side-emitting light source with a multi-reflection configuration in accordance with an embodiment of this disclosure.

Generally, gas sensors are designed to detect a specific type of gas or class of gases. For example, there are specific gas sensors designed to have sensitivity to specific gases such as carbon monoxide, carbon dioxide, nitrous oxide compounds, ammonia, methane, sulfur dioxide, hydrogen sulfide, methanol, ethanol, and volatile organic compounds. The signal generated by the interaction of gases with a sensor is related to the total concentration of all types of gases that the sensor can detect. In other words, a gas sensor may not be discriminatory with respect to the different gases that the sensor is able to detect at selected operating conditions since the total signal generated is a function of the responses from all detected gases. Therefore, a common approach for gas sensors is to design a sensor to detect a specific type of gas while minimizing sensitivity to other types of gases, or to provide a means to separate gas species and measure one at a time.

For applications in mobile devices and consumer devices, the size of a gas sensor can influence the sensitivity of the gas sensor with respect to gas concentrations available for analysis. For instance, an optical path length of radiation provided from a radiation source (e.g., one or more electromagnetic radiation sources) of a gas sensor can influence the detection limit of the gas sensor. Where the optical path length is relatively short, the gas sensor can be unable to provide accurate sensing of sensitive gas concentrations (e.g., gas concentrations in the parts-per-million (ppm) range).

Therefore, a gas concentration sensor is described having an integrated die-form light source and an integrated die-form infrared detector. In one or more implementations, the gas concentration sensor includes a package substrate defining at least one aperture, a gas permeable mesh (e.g., metallic mesh, GORE-TEX™) coupled to the package substrate and covering at least a portion of the at least one aperture, a die-form light source (e.g., heater, MEMS heater, LED, laser diode) positioned in an interior region of the package substrate, a die-form detector (e.g., thermopile, photodetector) positioned in the interior region of the package substrate, and control circuitry (e.g., ASIC) operably coupled to the die-form detector and the die-form light source and configured to detect and calibrate one or more signal outputs from the die-form detector to determine a gas concentration within the interior region of the package substrate. The gas concentration sensor can be configuration for specific detection of various gases through control of the spectral wavelengths emitted by the light source(s) and/or detected by the detector(s). Further the gas concentration sensor can be configured as a micro-optics package (e.g., an overall package form factor of about 4 mm×4 mm×2 mm or smaller) while maintaining an optical path suitable to achieve ppm-level concentration detection or to conform to design specifications.

Example Implementations

Referring to FIGS. 1A and 1B, a gas concentration sensor 100 is shown in accordance with example implementations of the present disclosure. As shown, the gas concentration sensor 100 includes a package substrate 102 (e.g., including a base portion 102a, one or more wall portions 102b, etc.), a gas-permeable mesh 104, a die-form light source 106 (e.g., at least one electromagnetic radiation source), a die-form detector 108, and control circuitry 110 (e.g., ASIC). The package substrate 102 at least partially encloses the die-form light source 106, the die-form detector 108, and the control circuitry 110 to provide a fully integrated gas concentration sensor 100. In embodiments, the package substrate 102 (and the associated base portion 102a and one or more wall portions 102b) comprises material that at least substantially prevents the transmission of radiation. For example, the package substrate 102 can comprise metal materials, metallic alloys, and ceramic materials, such as glass, $SiO_2$, AlN, $Al_2O_3$, and so forth. In embodiments, the package substrate is configured as a micro-optics package, such as a package having an overall package form factor of about 4 mm×4 mm×2 mm or smaller. The package substrate 102 defines an aperture 112 through which environmental gas can enter the package for analysis. For example, the one or more wall portions 102b can form the aperture 112 at a top portion of the gas concentration sensor 100, although other configurations can be provided. The gas permeable mesh 104 is generally coupled to the package substrate 102 (e.g., via adhesive or other coupling mechanism) such that at least a portion of the aperture 112 is covered by the gas permeable mesh 104. In embodiments, the gas permeable mesh 104 includes one or more of a metal mesh material, a GORE-TEX™ material, or other material permeable to one or more gases desired to be analyzed and reflective of light generated by the die-form light source 106.

In general, the die-form light source(s) 106 generates radiation 107 (e.g., electromagnetic radiation) for spectral absorption by gas within the package substrate 104. The radiation 107 is reflected (e.g., one or more wavelengths of electromagnetic radiation) within an interior region 105 of the package substrate 104, where a portion of the radiation can be lost due to spectral absorption by gas within the interior region 105, and where the radiation is subsequently detected by the die-form detector(s) 108 within the interior region 105. The spectral absorption is determined through analysis of the radiation detected by the die-form detector(s) 108, where such analysis can be facilitated by the control circuitry 108 (e.g., application specific integrated circuit (ASIC)). For example, the detection of gas concentration can be facilitated by comparison of radiation detected by different detectors 108 or by different wavelengths of a single detector 108. For instance, in an implementation a detector 108 can be chosen to avoid detection of spectral absorption band(s) of selected gas(es), where the detector 108 can compensate for changes or drifts in signal from other sources, such as air flow, temperature, light source intensity changes, etc. The die-form light source 106 can include, but is not limited to, an incandescent light source, a light emitting diode (LED), a laser diode, a vertical-cavity surface-emitting laser (VCSEL), and so forth. The sensitivity of the gas concentration sensor 100 can be controlled by varying one or more of the wavelengths of light emitted from the die-form light source(s) 106 and the sensitivity of the die-form detector(s) 108. In FIGS. 1A and 1B, the die-form light source 106 comprises a heater or broadband infrared light emitting diode (IR LED), where the sensitivity of the gas concentration sensor 100 is controlled at the die-form detector(s) 108. For example, the gas concentration sensor 100 of FIGS. 1A and 1B includes a first die-form detector 108a that is sensitive to a particular spectral absorption of a particular chemical of interest (e.g., $NO_x$, CO, $CO_2$, $H_2O$, or other gaseous chemical), and a second die-form detector 108b that serves as a reference channel to account for and/or compensate changes in light path, intensity changes of the die-form light source(s) 106, or other interferences (e.g., presence of another gas), and so forth. While two die-form detectors 108 are shown, the total number of die-form detectors 108 can vary (e.g., can be higher or lower), which can depend on the number and type of gases/liquids of interest.

The sensitivity of the die-form detector(s) 108 can be tailored depending on the type of detectors used. For example, the die-form detector(s) 108 can comprise one or more of a thermopile and a photodiode, where the sensitivity of a thermopile can be varied by integrating interference-based absorbers to the thermopile membrane area, and where sensitivity of a photodiode can be varied by integrating and/or depositing interference-based transmission filters on a surface of the photodiode. Further, the spectral sensitivity of the die-form detector(s) 108 can vary depending on the chemicals of interest to analyze with the gas concentration sensor 100. For example $CO_2$ has strong spectral absorption around 4.2 µm, therefor for $CO_2$ sensing applications one or more die-form detectors 108 (e.g., the first die-form detector 108a) can be configured to be sensitive to around 4.2 µm. A reference channel (e.g., the second die-form detector 108b) can be selected to avoid detecting absorptions of the gas(es) of interest. For example 3.9 µm can be a good candidate for many gas-sensing applications because gases such as $NO^x$, CO, $CO_2$, $H_2O$, and other prevalent atmosphere gases do not show strong absorption around it. For multiple gases of interest, the gas concentration sensor 100 can be configured with a die-form detector 108 for each gas of interest. For example, for a gas concentration sensor 100 directed to sensing $CO_2$ and CO, one detector or channel can be tuned to about 4.2 µm (for $CO_2$ sensitivity), one detector or can be tuned to about 4.6 µm (for CO sensitivity), and one detector or channel can be tuned to about 3.9 µm (as a reference channel).

The control circuitry 110 is coupled to the package substrate 102 (e.g., within the interior region 105) and is operably coupled to the die-form light source(s) 106 and the die-form detector(s) 108. In embodiments, the control circuitry 110 includes an application specific integrated circuit (ASIC). For example, the control circuitry 110 can compare the spectral radiation detected by the die-form detector(s) 108 with the spectral radiation emitted by the die-form light source(s) 106 to make determinations about the amount of spectral radiation absorption attributable to gas(es) present in the package substrate 102.

Referring to FIGS. 2A and 2B, a gas concentration sensor 200 is shown in accordance with example implementations of the present disclosure. Similar to the gas concentration sensors 100 shown with reference to FIGS. 1A and 1B, the gas concentration sensor 200 includes a package substrate 102, a gas-permeable mesh 104, a die-form light source 106, a die-form detector 108, and control circuitry 110. The gas concentration sensor 200 further includes one or more optical filters 202 positioned adjacent to (e.g., above) corresponding die-form detector(s) 108 to influence the sensitivity of the respective die-form detector(s) 108. For example, as shown in FIG. 2A, the gas concentration sensor 200 includes a first optical filter 202a positioned above the first die-form detector 108a and a second optical filter 202b positioned above the second die-form detector 108b. The first optical filter 202a and the second optical filter 202b can provide different filtering characteristics to provide different sensitivities to the respective die-form detectors 108. For example, the first optical filter 202a can filter for the spectral band of about 4.2 µm (e.g., for $CO_2$ sensitivity), whereas the second optical filter 202b can filter for the spectral band of about 3.9 µm (e.g., as a reference channel). In embodiments, the die-form detectors 108 are integrated within their own package, which can include a lid 204 (e.g., silicon lid, glass lid, etc.) positioned on package wall portions 206. The optical filters 202 can be applied to the lid 204, positioned above respective die-form detectors 108. The detector package can be hermetic. In embodiments, such as shown in FIG. 2C, the die-form light source(s) 106 can be included in a single package with the die-form detector(s) 108. For example, the lid 204 can extend to cover the die-form light source(s) 106, where a baffle 208 can be positioned between the die-form light source(s) 106 and the die-form detector(s) 108, such as to prevent or mitigate optical cross-talk.

Referring to FIGS. 3A and 3B, a gas concentration sensor 300 is shown in accordance with example implementations of the present disclosure. Similar to the gas concentration sensors 100 shown with reference to FIGS. 1A and 1B, the gas concentration sensor 300 includes a package substrate 102, a gas-permeable mesh 104, two or more die-form light sources 106, a die-form detector 108, and control circuitry 110. Further, the gas concentration sensor 300 establishes gas sensitivity through selection of particular die-form light sources 106. For example, the die-form light sources 106 include a first die-form light source 106a, configured to emit light having a first wavelength (e.g., 3.9 µm for a reference channel), and a second die-form light source 106b, configured to emit light having a second wavelength (e.g., 4.2 µm for $CO_2$ sensitivity). While two die-form light sources 106 are shown, additional die-form light sources can be included for differing spectral absorption bands for additional chemicals of interest, additional reference channels, and so forth. The die-form detector 108 of the gas concentration sensor 300 can include a broadband die-form detector 108, such as a broadband thermopile or broadband photodiode, to facilitate detection of the various wavelengths emitted by the die-form light sources 106.

Figure 4B:
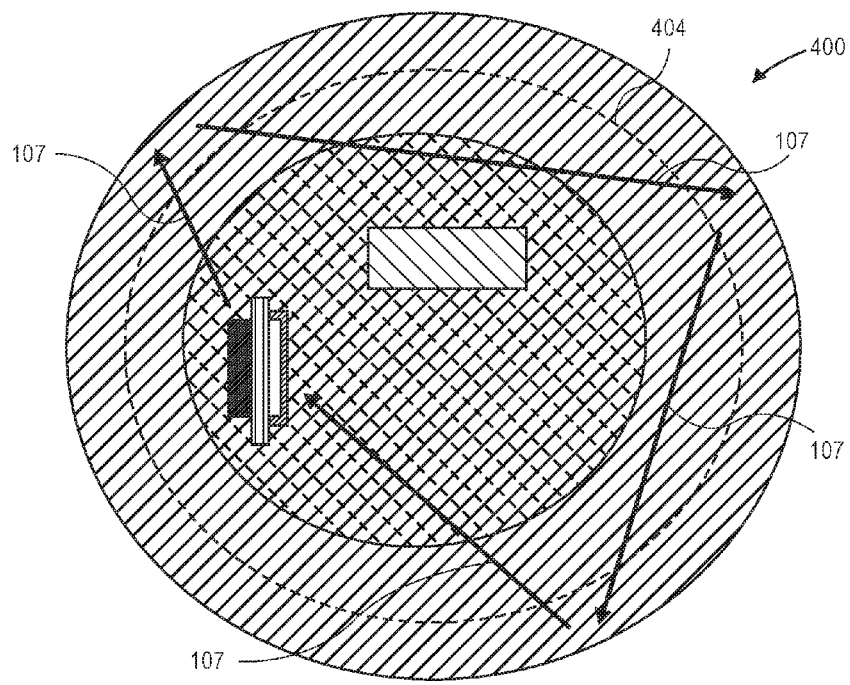
FIG. 4B illustrates a top view of the fully integrated gas concentration sensor of FIG. 4A.
Figure 4C:
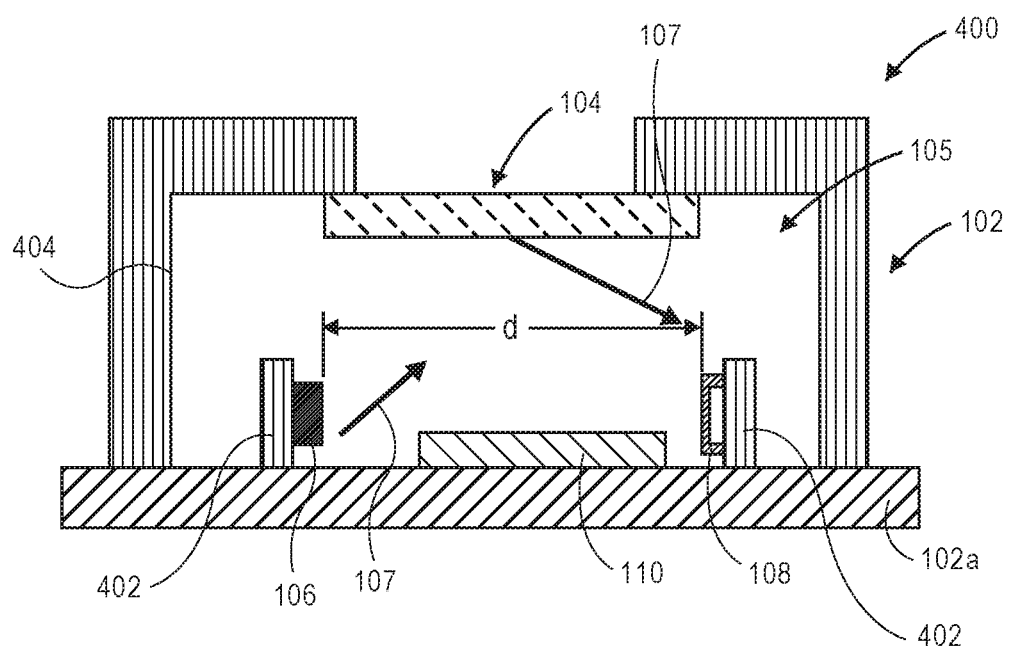
FIG. 4C illustrates a side view of a fully integrated gas concentration sensor having a side-emitting light source with a multi-reflection configuration in accordance with an embodiment of this disclosure.

Referring to FIGS. 4A and 4B, a gas concentration sensor 400 is shown in accordance with example implementations of the present disclosure. Similar to the gas concentration sensors 100 shown with reference to FIGS. 1A and 1B, the gas concentration sensor 400 includes a package substrate 102, a gas-permeable mesh 104, a die-form light source 106, a die-form detector 108, and control circuitry 110. The orientation of the die-form light source 106 within the package substrate 102 can be varied to influence the optical path traveled by radiation 107 emitted from the die-form light source 106. For example, the die-form light source 106 can be positioned substantially parallel to the base portion 102a (e.g., see FIG. 4A), such as coupled to a substantially vertical support wall 402, which separates the die-form light source 106 from the die-form detector 108 (e.g., opposing each other). For example, each of the die-form light source 106 and the die-form detector 108 can be coupled to the substantially vertical support wall 402 (e.g., see FIG. 4A)

such that the die-form light source 106 and the die-form detector 108 face away from each other (e.g., the radiation 107 from the die-form light source is initially directed away from the die-form detector 108, prior to reflection within the interior region 105). Further, the package substrate 102 can include one or more curved surfaces 404 defining the interior region 105 for optical performance enhancement of the gas concentration sensor 400 (e.g., to facilitate reflection of the radiation 107 within the interior region 105). As another example, the die-form light source(s) 106 and the die-form detector(s) 108 can be positioned to face each other (e.g., see FIG. 4C), where the gas concentration sensor 400 includes a distance d between the respective die-form light source(s) 106 and die-form detector(s) 108, such as to permit the passage of gas(s) within the interior region 105 of the package substrate 102. In embodiments, one or more of the die-form light source 106 and the die-form detector 108 can be provided in a separate package within the interior region 105 of the package substrate 102 (e.g., package wall portions 206 with lid shown in FIG. 4A; package wall portions 206 with tunable filter 502 described with reference to FIGS. 5A-5D; etc.). In other examples, the die-form light source 106 can be positioned substantially perpendicularly to the base portion 102a (e.g., see FIG. 1A).

Figure 5C:
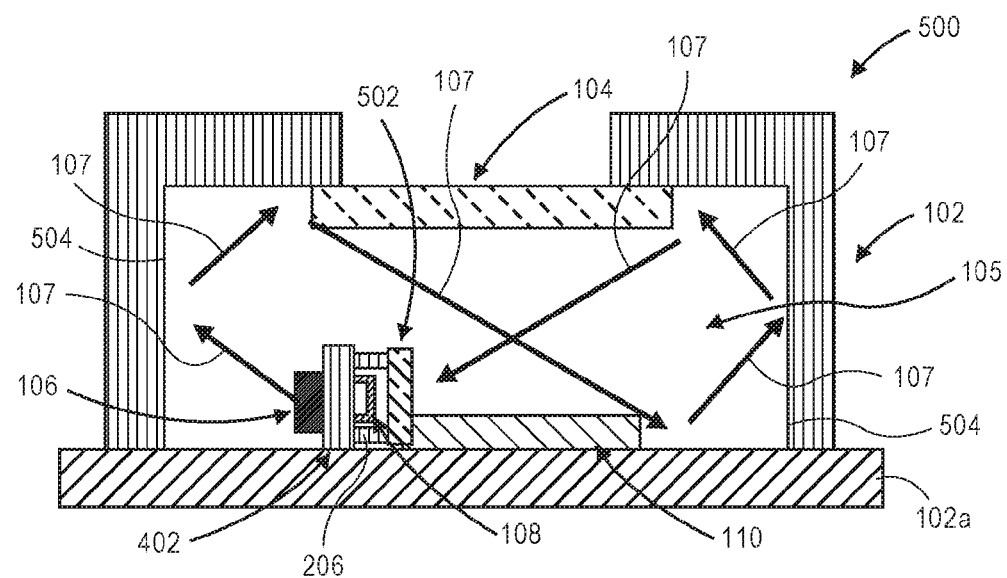
FIG. 5C illustrates a side view of a fully integrated gas concentration sensor having a side-emitting light source and a tunable filter adjacent a broadband detector with a multi-reflection configuration in accordance with an embodiment of this disclosure.
Figure 5D:
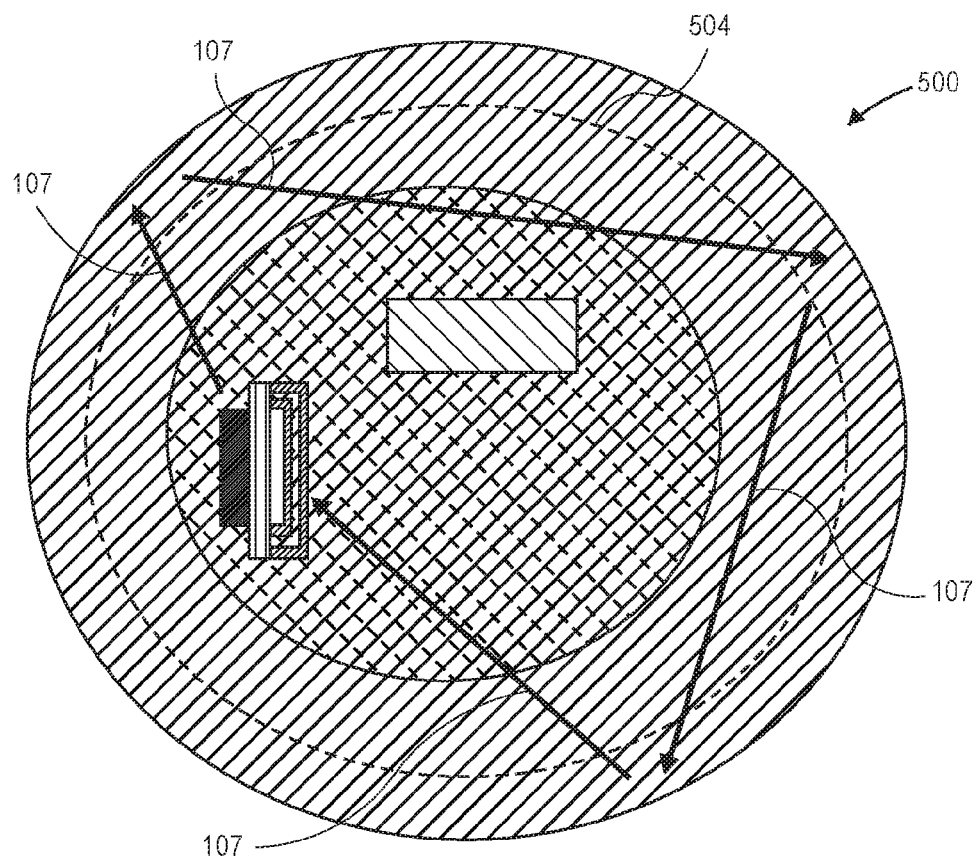
FIG. 5D illustrates a top view of the fully integrated gas concentration sensor of FIG. 5C.

Referring to FIGS. 5A and 5B, a gas concentration sensor 500 is shown in accordance with example implementations of the present disclosure. Similar to the gas concentration sensors 100 shown with reference to FIGS. 1A and 1B, the gas concentration sensor 500 includes a package substrate 102, a gas-permeable mesh 104, a die-form light source 106, a die-form detector 108, and control circuitry 110. The die-form light source 106 and the die-form detector 108 of the gas concentration sensor 500 are broadband components, where the sensitivity of the gas concentration sensor 500 is selected by a tunable filter 502 positioned adjacent (e.g., above) the die-form detector 108. For example, the tunable filter 502 can comprise a high resolution, tunable Faby-Perot filter or grating. The tunable filter 502 can provide a plurality of spectral channels (e.g., up to one hundred channels in embodiments) for detection by the die-form detector 108, while maintaining as few as one die-form light source 106 and one die-form detector 108. As such, the tunable filter 502 can facilitate detection of organic gases (e.g., acetone) or other chemicals having complex IR-spectral absorption characteristics or fingerprints. In embodiments, the control circuitry 110 controls the filtering characteristics of the tunable filter 502. For example, the control circuitry 110 can include an ASIC to apply an electrostatic current to the tunable filter 502 to dictate which wavelength of radiation can pass through the tunable filter 502 for detection by the die-form detector 108. In embodiments, the die-form light source 106 and the die-form detector 108 (with associated tunable filter 502) can be oriented within the interior region 105 of the package substrate 102 to influence the optical path traveled by the radiation, such as shown in FIGS. 5C and 5D, where the die-form light source 106 is positioned substantially parallel to the base portion 102a, coupled to the substantially vertical support wall 402. Further, the package substrate 102 can include one or more curved surfaces 504 (e.g., shown in FIGS. 5C and 5D) defining the interior region 105 for optical performance enhancement of the gas concentration sensor 500 (e.g., to facilitate reflection of the radiation 107 within the interior region 105).

Figure 6:
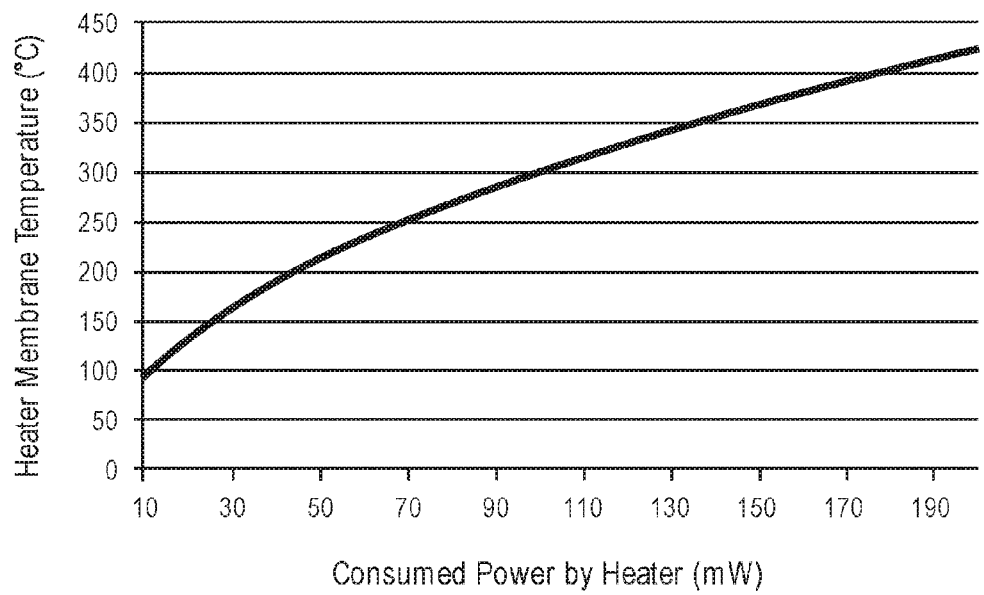
FIG. 6 illustrates a chart of heater temperature versus electrical power consumption for an example MEMS heater.

The gas concentration sensors described herein can be configured as micro-optics packages (e.g., an overall package form factor of about 4 mm×4 mm×2 mm or smaller), while maintaining an optical path suitable to achieve ppm-level concentration detection or to conform to design specifications. However, when integrating die-level light sources and detectors into a small package, reaching design detection limits can be a challenge particularly when taking into account design trade-offs. For example, in one configuration, a MEMS heater can be utilized as the light source where the following relationship can exist:

$$T_{heater} = f(W_{heater}) \qquad \text{equation 1}$$

where $T_{heater}$ is the average temperature of a heater membrane and $W_{heater}$ is electrical power consumed by the heater. For many applications, minimizing the amount of electrical power consumption is advantageous, such as to extend battery life time. An example relationship of heater temperature and electrical power consumption is provided in FIG. 6. For many applications, a power consumption of <10 mW can extend battery life time. As it can be noted from FIG. 6, the membrane is not significantly heated for low powers and thus optical power will be very small. To compensate, in an embodiment the light source utilizes a pulsed current through the IR heater to have temporary power with a higher power consumption, but in average have a low power consumption, which can result in an extended battery life time. In one example, the current or voltage is pulsed to the heater with a 20% duty cycle to provide a peak power of 50 mW and average of 10 mW. At peak of the excitation of the current or voltage through the heater with a peak power of 50 mW, the temperature of the heater membrane will reach about 200° C. Higher peak temperatures in the membrane can be an important consideration since the optical power from the heater is proportional to temperature to the exponent of 4 from Stephan Boltzmann law, as provided below:

$$P_{out-total} \propto T^4 \qquad \text{equation 2}$$

Optical power output of the heater in a specific spectral band centered at $\lambda_0$ with bandwidth of $\Delta$ can be calculated as:

$$P_{out-\lambda_0} \propto \pi \int_{\lambda_0-\Delta/2}^{\lambda_0+\Delta/2} B(\lambda, T) d\lambda \qquad \text{equation 3}$$

where $$B(\lambda, T) = \frac{2hc^2}{\lambda^5 \left(\exp\left(\frac{hc}{\lambda kT}\right) - 1\right)}$$

is a plank function for brightness.

Optical power received at the detector with a filter center at $\lambda_0$ and bandwidth of $\Delta$ can be calculated according to Beer-Lambert law:

$$P_{detector} \propto P_{out-\lambda_0} \cdot \exp(-\alpha(\lambda_0)d) \qquad \text{equation 4}$$

where $\alpha(\lambda_0)$ is absorption coefficient of the surrounding gas at wavelength $\lambda_0$ and d is average path length that light travels between light source and detector in the gas medium. Absorption coefficient can depend on the concentration of the gas or gases in the medium, for example in case of one gas that has $\alpha(\lambda_0)$ absorption at wavelength $\lambda_0$ with 100% concentration, absorption vs concentration can follow the following equation at other concentrations when the other gas has absorption of $\beta(\lambda_0)$ at wavelength $\lambda_0$:

Absorption($\lambda_0$,concentration)=concentration·$\alpha(\lambda_0)$+
(1−concentration)·$\beta(\lambda_0)$      equation 5

In the case that $\beta(L_0)=0$ then:

Absorption($\lambda_0$,concentration)=concentration·$\alpha(\lambda_0)$      equation 6

With this, equation 4 can be provided as:

$P_{detector}=A_{heater}F_{heater-detector}\cdot P_{out-\lambda_0}\cdot\exp(-\text{concentration}.\alpha(\lambda_0)d)$      equation 7 where in this case $\alpha(\lambda_0)$ is absorption at 100% concentration and there is no other gas absorption light at wavelength $\lambda_0$, and where $F_{heater-detector}$ is a view factor of light source to detector (e.g., showing how much of light emitted from light source reaches the detector, which can depend on package geometry and placement of emitter and detector with respect to each other), and where $\lambda_{heater}$ is an area of the heater light source.

The output signal of the detector can be provided as:

$V_{detector}=R\cdot P_{detector}$      equation 8 where R is responsivity of the detector in units of V/W.

Figure 7:
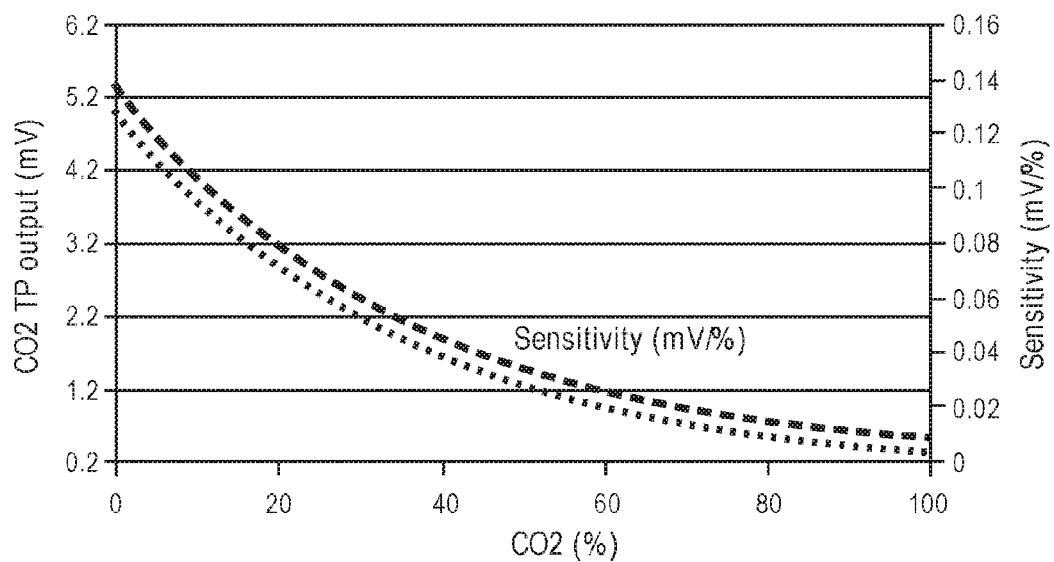
FIG. 7 illustrates a chart of output signal of a detector versus concentration of a gas of interest in accordance with an embodiment of this disclosure.

Using equations 1 through 8, the output signal of the detector versus concentration of the gas of interest can be calculated and plotted, an example of which is provided in FIG. 7. The dotted line shows the output of the detector versus concentration levels of carbon dioxide. The derivative of this curve versus the concentration can provide the sensitivity of change of output signal for unit change in concentration level, which is shown in FIG. 7 with a dashed line (the units could be, for example, mV per %).

Each detector can include noise in the respective readout (e.g., for a thermopile it is thermal or Johnson noise). The total noise from the detector can be calculated from the following equation:

$V_{noise-total}=\sqrt{V_{noise-detector}^2+V_{noise-readout}^2}$      equation 9 where $V_{noise-readout}$ can be provided by a specification of an available readout, which is given per unit of bandwidth, such by the following example:

$V_{noise-readout}=40\ nV/\sqrt{Hz}$      equation 10 where $V_{noise-detector}$ depends on the resistance of the detector, which in the case of a thermopile is given by:

$V_{noise-detector}=\sqrt{4kTR}/\sqrt{Hz}$      equation 11

Based on equations 10 and 11, the noise is dependent on the bandwidth of the measured signal or in other words how long the measurement takes place (e.g., integration time). If integration time or measurement time is $\tau$ then the bandwidth of signal is $B=1/\tau$ and from equations 10 and 11 the noise of readout and detector based on measurement time would be:

$V_{noise-readout}=40\ nV\sqrt{1/\tau}$      equation 12

$V_{noise-detector}=\sqrt{4kTR}\sqrt{1/\tau}$      equation 13

Figure 8:
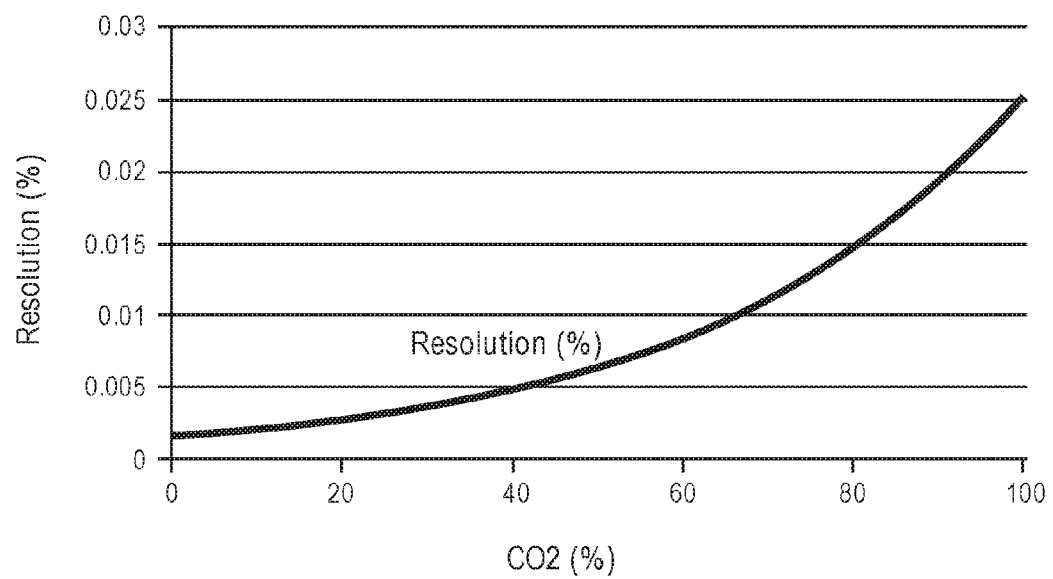
FIG. 8 illustrates a chart of resolution versus percentage of carbon dioxide in accordance with an embodiment of this disclosure.

Based on the noise and sensitivity described herein above, the resolution of the system can be calculated. For example, the resolution can be provided by noise divided by sensitivity. Since noise has units directed to volts and sensitivity has units of V/(%), the units of resolution would be percentage (%). An example graph of resolution versus percentage of carbon dioxide is provided in FIG. 8.

Sampling rate of the signal is duty cycle determined earlier based on power consumption limit divided by integration time:

$$\text{Sampling Rate} = \frac{\text{duty cycle}}{\tau}$$      equation 14

Example Methods

Figure 9:
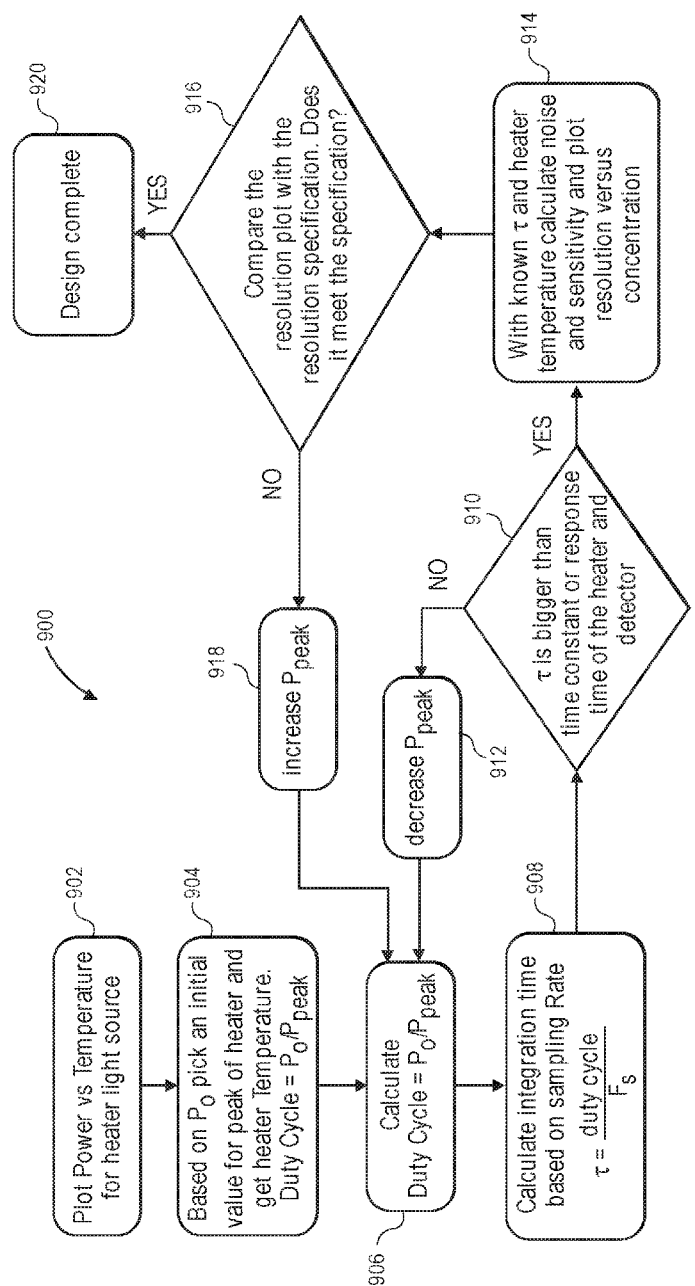
FIG. 9 illustrates a flow chart of a method for designing a gas concentration sensor in accordance with an embodiment of this disclosure.

Referring to FIG. 9, a method 900 for designing a gas concentration sensor is provided in accordance with an example embodiment of the present disclosure. The method 900 includes plotting power versus temperature for a heat-based light source (e.g., a MEMS heater) (Block 902). Then, based on a desired average power consumption, select an initial value for peak power of the heater and determine the associated heater temperature (Block 904). The method 900 further includes calculating the duty cycle, where the duty cycle=$P_0/P_{peak}$ (Block 906). The method 900 further includes calculating integration time based on the sampling rate (e.g., via equation 14) (Block 908). The method 900 further includes determining whether the integration time is larger than a time constant or a response time of the heater and detector (Block 910). If the determination in Block 910 is no (i.e., the integration time is less than the time constant or the response time of the heater and detector), then the method 900 continues to Block 912, where the peak power is decreased, and then flows back to Block 906. If the determination in Block 910 is yes (i.e., the integration time is larger than the time constant or the response time of the heater and detector), then the method 900 continues to Block 914, where the method 900 further includes calculating noise and sensitivity and plotting resolution versus concentration for a given integration time and heater temperature. The method 900 further includes comparing the resolution plot with the desired resolution to determine whether the resolution from the resolution plot meets the desired resolution (Block 916). If the determination in Block 916 is no (i.e., the resolution from the resolution plot does not meet the desired resolution), then the method 900 continues to Block 918, where the peak power is increased, and then flows back to Block 906. If the determination in Block 916 is yes (i.e., the resolution from the resolution plot meets the desired resolution), then the method 900 finishes at Block 920 (e.g., the design is complete).

Tube-Based Gas Flow Example Implementations

Figure 10A:
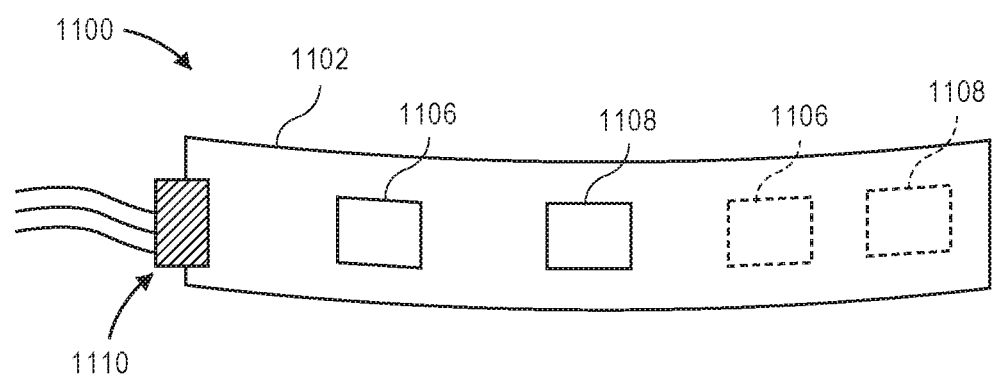
FIG. 10A illustrates a gas concentration sensor with a flexible substrate in accordance with an embodiment of this disclosure.
Figure 10B:
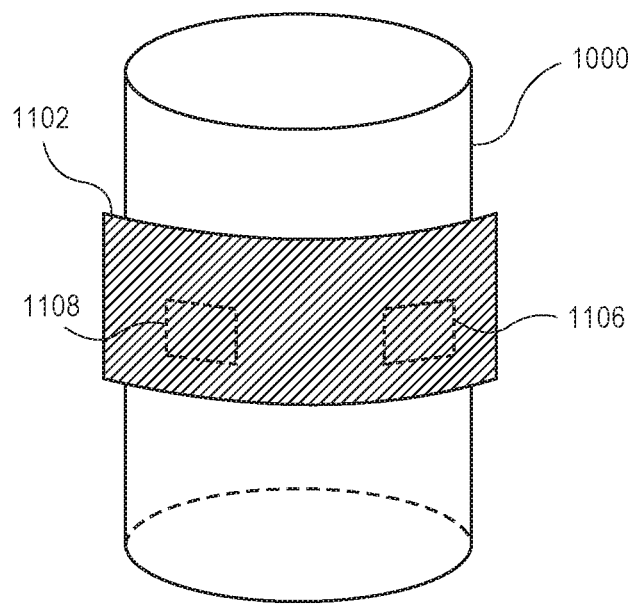
FIG. 10B illustrates the gas concentration sensor of FIG. 10A positioned about a substantially cylindrical object.
Figure 10C:
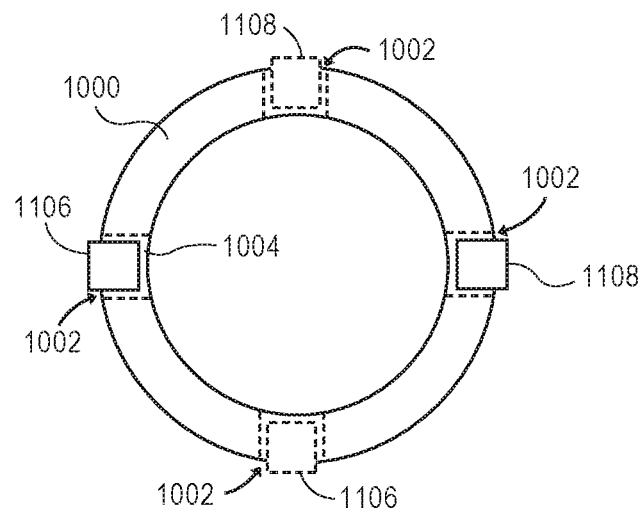
FIG. 10C illustrates a cross-sectional view of a gas concentration sensor with an interior region through which gas can travel in accordance with an embodiment of this disclosure.

Referring to FIGS. 10A-10G and FIG. 11, a gas concentration sensor 1100 is shown in accordance with example implementations of the present disclosure. As shown in FIG. 10A, the gas concentration sensor 1100 can include a flexible substrate 1102, one or more light sources 1106 (e.g., one or more die-form light sources, such as a MEMS heater, an LED, or the like), one or more detectors 1108 (e.g., one or more die-form detectors, such as an IR detector, an IR thermopile, a photodiode, or the like), and a connector portion 1110. The detector(s) 1108 and/or the light source(s) 1106 can include one or more filters configured to restrict light to wavelengths of interest for emission and/or for detection. The flexible substrate 1102 can conform to a structure through which gas can flow (e.g., air tubing) to facilitate measurement of gas concentrations by the light source(s) 1106 and the detector(s) 1108. For example, as shown in FIG. 10B, the flexible substrate can be coupled about a tubular object 1000 through which gas can flow. While the object 1000 is shown as being substantially cylindrical, it is noted that the flexible substrate 1102 can conform to other tubular shapes and/or surface structures, including but not limited to, rectangular surfaces, spherical surfaces, irregular surfaces, patterned surfaces, and the like, where gas can flow through the tubular structure for analysis by the gas concentration sensor 1100. In implementations, the object 1000 is constructed of an IR-transmissive material to permit the transmission of light from the light source(s) 1106 and to permit the subsequent reception of the light by the detector(s) 1108. For example, when the flexible substrate 1102 is positioned about the object 1000, the light source(s) 1106 and the detector(s) 1108 are brought into contact with the object 1000 (e.g., on an outer surface of the object) to permit transmission of light by the light source(s) 1106 toward an interior region of the object 1000 and to permit reception of the light by the detector(s) 1108 reflected, scattered, etc. from the interior region of the object 1000 for detection of gas concentration within the object 1000. The connector portion 1110 includes circuitry, wiring, or the like, to facilitate operation of the light source(s) 1106 and the detector(s) 1108. For example, the connector portion 1100 can include circuitry, wiring, or the like to provide power to and actuate/drive the light source(s) 1106 and the detector(s) 1108, to receive data signals from the detector(s) 1108, and so forth.

In implementations, the object 1000 forms the substrate for the gas concentration sensor 1100. For example, referring to FIG. 10C, the object 1000 defines a plurality of cavities 1002 into which the light source(s) 1106 and the detector(s) 1108 can be positioned. The cavities 1002 can be individually shaped to correspond to the individual shapes/dimensions of the respective light source(s) 1106 and detector(s) 1108 positioned within the cavities 1002. In implementations, the cavities 1002 extend through the material of the object 1000 to provide a channel into which the light source(s) 1106 and the detector(s) 1108 can be positioned. In such a configuration, the light source(s) 1106 and the detector(s) 1108 can be sealed (e.g., via adhesive, epoxy, or other sealant) into position to provide an air-tight seal, or can be constructed to provide an air-tight friction-fit between the respective light source(s) 1106 and detector(s) 1108 and the portion of the object 1000 forming the cavities 1002 to provide an air-tight seal without additional sealant. In implementations, the cavities 1002 do not fully extend through the material of the object 1000. For example, the object 1000 can include a transparent portion 1004 (e.g., a transparent window material) defining an edge of the cavities 1002 adjacent the interior portion of the object 1000. The transparent portion 1004 can permit light emitted from the light source(s) 1106 to enter the interior portion of the object 1000 (e.g., to interact with gas(es) therein) and can permit the detector(s) 1108 to receive at least a portion of the light emitted from the light source(s) 1106.

Figure 10D:
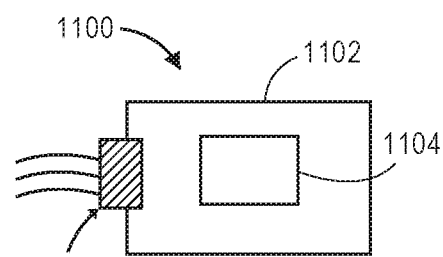
FIG. 10D illustrates a portion of a gas concentration sensor for coupling with an object in accordance with an embodiment of this disclosure.
Figure 10E:
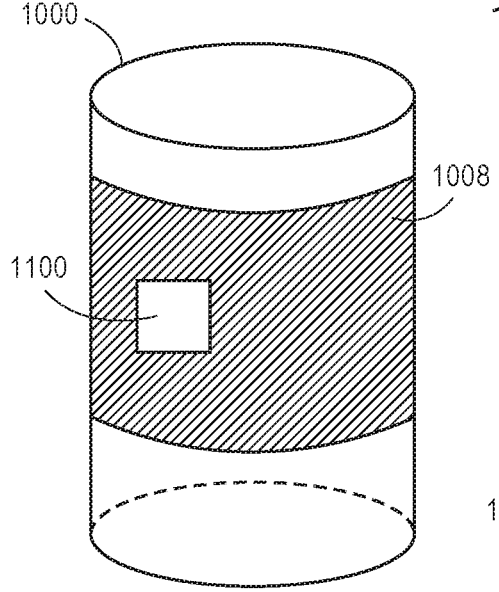
FIG. 10E illustrates a gas concentration sensor with an object having a reflective interior surface in accordance with an embodiment of this disclosure.
Figure 10F:
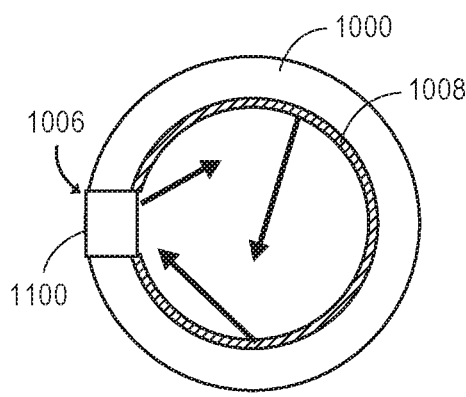
FIG. 10F illustrates a cross-sectional view of the gas concentration sensor of FIG. 10E.
Figure 10G:
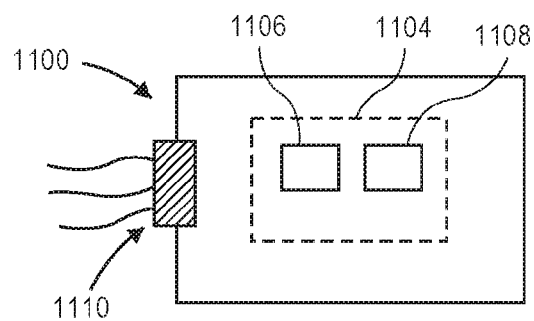
FIG. 10G illustrates a portion of a gas concentration sensor for coupling with an object in accordance with an embodiment of this disclosure.

Referring to FIGS. 10D-10F, in implementations the gas concentration sensor 1100 includes a substrate 1102 (e.g., flexible substrate) having a nondispersive infrared sensor (NDIR sensor) 1104 affixed thereto for coupling with the object 1000. For example, the object 1000 can define an opening or aperture 1006 into which the sensor 1104 can be placed for transmitting light into the interior region of the object 1000 and for receiving reflected, scattered, etc. light from the interior region of the object 1000 to determine a concentration of chemical specie(s) of the gas within the interior region of the object 1000. The sensor 1104 can include one or more light source(s) 1106 and one or more detector(s) 1108 (e.g., as shown in FIG. 10G), where the light source(s) 1106 and the detector(s) 1108 can be provided in different structural packages positioned relative to one another, or can be provided in the same structural package. In an implementation, the object 1000 includes a reflective coating 1008 on a surface of the interior region of the object 1000 (e.g., as shown in FIG. 10F). The reflective coating 1008 can provide a reflective surface against which light emitted from the light source(s) 1106 can reflect for subsequent detection by the detector(s) 1108. In an implementation, the opening or aperture 1006 is sized according to the size characteristics of the sensor 1104, such that the sensor 1104 can securely fit within the opening or aperture 1006, such as by providing an air-tight fit, a friction fit requiring little to no accompanying sealant, or the like. Accordingly, the substrate 1102 may not be positioned about the entire circumference of the object 1000 in order to secure the sensor 1104 in position.

Figure 11:
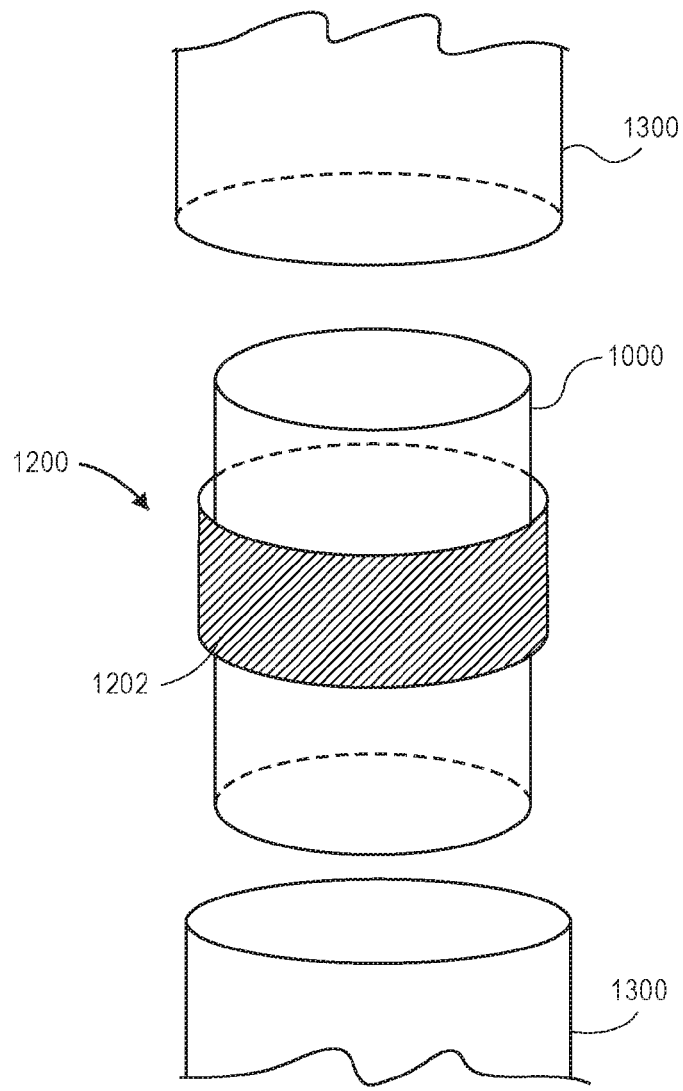
FIG. 11 illustrates a gas concentration sensor module having a cover portion for coupling to sources of gas in accordance with an embodiment of this disclosure.

Referring to FIG. 11, a gas concentration sensor module 1200 having a cover portion 1202 for coupling to sources of gas in accordance with an embodiment of this disclosure is provided. In implementations, the gas concentration sensor module 1200 includes a gas concentration sensor (e.g., one or more of the sensors 1100 described herein) and the cover portion 1202 for holding or positioning the gas concentration sensor relative to the object 1000 through which gas can flow. The gas concentration sensor module 1200 can also include, but is not limited to, read out electronics (e.g., ASIC), wireless or wired electronics to facilitate communication of data to and from the gas concentration sensor module 1200, and the like. Such data can include real time end-tidal carbon dioxide data ($EtCO_2$ data), concentration versus time data for carbon diode, another gas, a plurality of gases, or combinations thereof. The gas concentration sensor module 1200 can be positioned within or connected to a tube 1300, which can be part of a tubing network to provide the source of gas to be measured. For example, the gas concentration sensor module 1200 can be connected to or positioned within respiratory tubes associated with a patient to monitor and detect carbon dioxide or other gases (e.g., acetone—such as for early detection of diabetes) present in the patient's breath. Alternatively, the individual can breathe directly into the tube 1300 for direct analysis of the expired breath. Thus, gas can be provided from the tube 1300 (directly or indirectly) into the interior portion of the object for measurement of the gas concentration(s) by the light source(s) 1106 and the detector(s) 1108 associated with the gas concentration sensor 1100 of the gas concentration sensor module 1200.

It should be recognized that the various functions, operations, or steps described throughout the present disclosure may be carried out by any combination of hardware, software, or firmware. In some embodiments, various steps or functions are carried out by one or more of the following: electronic circuitry, logic gates, multiplexers, a programmable logic device, an application-specific integrated circuit (ASIC), a controller/microcontroller, or a computing system. A computing system may include, but is not limited to, a personal computing system, mainframe computing system, workstation, image computer, parallel processor, or any other device known in the art. In general, the terms "controller" and "computing system" are broadly defined to encompass any device having one or more processors, which execute instructions from a carrier medium.

Program instructions implementing methods, such as those manifested by embodiments described herein, may be transmitted over or stored on carrier medium. The carrier medium may be a transmission medium, such as, but not limited to, a wire, cable, or wireless transmission link. The carrier medium may also include a non-transitory signal bearing medium or storage medium such as, but not limited to, a read-only memory, a random access memory, a magnetic or optical disk, a solid-state or flash memory device, or a magnetic tape.

It is further contemplated that any embodiment of the disclosure manifested above as a system or method may include at least a portion of any other embodiment described herein. Those having skill in the art will appreciate that there are various embodiments by which systems and methods described herein can be implemented, and that the implementation will vary with the context in which an embodiment of the disclosure is deployed. Furthermore, it is to be understood that the present application is defined by the appended claims. Although embodiments of the present application have been illustrated, it is apparent that various modifications may be made by those skilled in the art without departing from the scope and spirit of the disclosure.

What is claimed is:

1. A gas concentration sensor, comprising:
   a package substrate defining at least one aperture, the package substrate including a base portion and a substantially vertical support wall extending from the base portion;
   an electromagnetic radiation source positioned in an interior region of the package substrate coupled to the substantially vertical support wall; and
   a detector positioned in the interior region of the package substrate and coupled to the substantially vertical support wall opposite the electromagnetic radiation source, the detector configured to receive at least a portion of electromagnetic radiation generated by the electromagnetic radiation source to determine a gas concentration within the interior region of the package substrate.

2. The gas concentration sensor of claim 1, further comprising:
   control circuitry coupled to the package substrate and operably coupled to the detector and configured to detect and calibrate one or more signal outputs from the detector to determine the gas concentration within the interior region of the package substrate.

3. The gas concentration sensor of claim 1, wherein the detector includes a first detector sensitive to a first spectral absorption wavelength and a second detector sensitive to a second spectral absorption wavelength.

4. The gas concentration sensor of claim 3, wherein the second spectral absorption wavelength is a reference channel.

5. The gas concentration sensor of claim 3, where the detector includes a filter positioned adjacent the first detector to filter electromagnetic radiation detectable by the first detector and includes a second filter positioned adjacent the second detector to filter electromagnetic radiation detectable by the second detector.

6. The gas concentration sensor of claim 5, further comprising a lid positioned above the first detector and the second detector.

7. The gas concentration sensor of claim 6, wherein the first filter and the second filter are coupled to the lid.

8. The gas concentration sensor of claim 1, wherein the detector is provided in a separate package within the interior region of the package substrate.

9. The gas concentration sensor of claim 1, wherein the electromagnetic radiation source and the detector are provided in a separate package within the interior region of the package substrate.

10. The gas concentration sensor of claim 1, wherein the electromagnetic radiation source includes a first electromagnetic radiation source configured to emit electromagnetic radiation having a first wavelength and a second electromagnetic radiation source configured to emit electromagnetic radiation having a second wavelength.

11. The gas concentration sensor of claim 1, wherein the electromagnetic radiation source is positioned substantially parallel to a base portion of the package substrate.

12. The gas concentration sensor of claim 1, wherein the substrate includes one or more curved surfaces defining the interior region for optical performance enhancement of the gas concentration sensor.

13. The gas concentration sensor of claim 1, wherein the electromagnetic radiation source is oriented to face away from the detector.

14. The gas concentration sensor of claim 1, wherein one or more surfaces of the substrate within the interior region are reflective of one or more wavelengths of interest of the electromagnetic radiation.

15. The gas concentration sensor of claim 1, wherein the detector includes a tunable filter.

16. The gas concentration sensor of claim 15, wherein the tunable filter includes a Faby-Perot filter.

17. The gas concentration sensor of claim 15, wherein the control circuitry is configured to control one or more filtering characteristics of the tunable filter.

18. The gas concentration sensor of claim 1, further comprising:
   a gas permeable mesh coupled to the package substrate and covering at least a portion of the at least one aperture.

19. The gas concentration sensor of claim 18, wherein the gas permeable mesh includes at least one of a metallic mesh or a GORE-TEX mesh.

20. A gas concentration sensor, comprising:
   a tubular structure having an interior region through which gas can flow;
   an electromagnetic radiation source coupled to a flexible substrate and coupled to the tubular structure and configured to direct electromagnetic radiation to the interior region of the tubular structure; and
   a detector coupled to the flexible substrate and coupled to the tubular structure and positioned to receive at least a portion of electromagnetic radiation generated by the electromagnetic radiation source to determine a gas concentration within the interior region of the tubular structure.

* * * * *